United States Patent

Faasse, Jr.

[11] Patent Number: 5,153,040
[45] Date of Patent: * Oct. 6, 1992

[54] WOUND DRESSING

[75] Inventor: Adrian L. Faasse, Jr., Middleville, Mich.

[73] Assignee: Minnesota Mining and Manufacturing Co., St. Paul, Minn.

[*] Notice: The portion of the term of this patent subsequent to Sep. 25, 2007 has been disclaimed.

[21] Appl. No.: 383,229

[22] Filed: Jul. 19, 1989

Related U.S. Application Data

[63] Continuation of Ser. No. 3,778, Jan. 16, 1987, abandoned, which is a continuation of Ser. No. 710,409, Mar. 11, 1985, abandoned.

[51] Int. Cl.$^5$ .......................... C09J 7/02; A61F 13/02
[52] U.S. Cl. ........................................ 428/40; 428/41; 428/131; 428/132; 428/137; 428/192; 428/343; 428/352; 428/354; 602/54; 602/57
[58] Field of Search .................. 428/40, 41, 131, 132, 428/137, 192, 343, 352, 354; 128/155, 156

[56] References Cited

U.S. PATENT DOCUMENTS

| Re. 33,353 | 9/1990 | Heinecke | 428/40 |
|---|---|---|---|
| 2,273,873 | 2/1942 | Klein | 128/156 |
| 2,646,040 | 7/1953 | Stanton | 128/155 |
| 2,712,312 | 7/1955 | Deker et al. | 128/156 |
| 2,734,503 | 2/1956 | Doyle | 128/156 |
| 2,870,129 | 1/1959 | Merriam | 128/156 |
| 2,949,443 | 8/1960 | Merriam et al. | 128/156 |
| 2,969,057 | 1/1961 | Simmons | 128/2 |
| 3,402,716 | 9/1968 | Baxter | 128/335 |
| 3,426,754 | 2/1969 | Bierenbaum | 128/260 |
| 3,457,919 | 7/1969 | Harbard | 128/156 |
| 3,645,835 | 2/1972 | Hodgson | 161/196 |
| 3,885,560 | 5/1975 | Baldwin | 128/214 R |
| 4,080,969 | 3/1978 | Casey et al. | 128/156 |
| 4,163,822 | 8/1979 | Walter | 428/304 |
| 4,176,664 | 12/1979 | Kalish | 128/156 |
| 4,192,299 | 3/1980 | Sabatano | 128/155 |
| 4,245,630 | 1/1981 | Lloyd et al. | 128/155 |
| 4,275,721 | 6/1981 | Olson | 128/133 |
| 4,340,043 | 7/1982 | Seymour | 128/132 D |
| 4,370,981 | 2/1983 | Sanderson | 128/334 |
| 4,379,881 | 4/1983 | Peck | 524/561 |
| 4,413,621 | 11/1983 | McCracken et al. | 128/156 |
| 4,414,970 | 11/1983 | Berry | 128/156 |
| 4,418,822 | 12/1983 | Dotta | 206/441 |
| 4,420,519 | 12/1983 | Slemmons | 428/40 |
| 4,452,845 | 6/1984 | Lloyd et al. | 428/220 |
| 4,513,739 | 4/1985 | Johns | 128/156 |
| 4,598,004 | 7/1986 | Heinecke | 428/40 |

OTHER PUBLICATIONS

Catalog Sheet entitled "Wound Dressings By the Dozen".

Primary Examiner—Kriellion S. Morgan
Attorney, Agent, or Firm—Gary L. Griswold; Walter N. Kirn; Dale A. Bjorkman

[57] ABSTRACT

A wound dressing includes a transparent vapor and gas permeable polymeric film which has an adhesive coated surface. A pair of liners or release sheets cover the adhesive coated surface and the liners define overlapping gripping flaps. Additional adhesive strips are positioned at opposed edges of the film and interposed between the adhesive coated surface of the film and the liners. Increased adhesion of the film to the liners occurs at the adhesive strips. The film is perforated adjacent the adhesive strips.

10 Claims, 2 Drawing Sheets

WOUND DRESSING

This is a continuation of application Ser. No. 07/003,778 filed Jan. 16, 1987, now abandoned, which is a continuation of application Ser. No. 06/710,409, filed Mar. 11, 1985, now abandoned.

BACKGROUND OF THE INVENTION

The present invention relates to bandages, wound dressings, surgical dressings, transdermal dressings, topical dressings and the like. While not so limited, the invention is especially suited for use in dressings which include a vapor and gas permeable polymeric film having an adhesive coated surface.

Various forms of bandages or dressings have heretofore been proposed, including dressings formed from transparent polymeric films which are coated with a biocompatible or hypoallergenic pressure-sensitive adhesive. Such dressings have many uses. For example, they are used for skin closures, wound covers, pressure sore covers and intravenous fluid site covers.

A typical film type dressing is formed from a polyurethane film which is permeable to oxygen and water vapor. Commercially available polyurethane films usable as dressings have moisture vapor transmission rates between 15 and 80 grams per 100 square inches per 24 hours as determined by ASTM Test E 96 at 100° F. and 90 percent relative humidity. The films have a thickness of from 1 to 3 mils.

Various types of pressure sensitive adhesive are used to retain the film on the skin of the patient. The well-known skin contact adhesives are copolymers of 2-ethylhexyl acrylate and vinyl acetate. Water based adhesives and hot melt adhesives may also be employed. The adhesive is coated or spread onto the film at a thickness so as not to impede the gas vapor permeability characteristics of the film. Generally, the adhesive coated film is applied to a silicone-coated carrier, release sheet or liner. Typically, the dressings are supplied in different sizes in individually sterilized packages. Examples of various transparent film-type wound or surgical dressings may be found in U.S. Pat. No. 4,413,621 entitled FILM DRESSING and issued on Nov. 8, 1983 to McCracken et al; U.S. Pat. No. 4,370,981 entitled PROTECTIVE DEVICES AND METHOD and issued on Feb. 1, 1983 to Sanderson; U.S. Pat. No. 3,426,754 entitled BREATHABLE MEDICAL DRESSING and issued on Feb. 11, 1969 to Bierenbaum et al; and U.S. Pat. No. 2,949,443 entitled SURGICAL DRESSINGS and issued on Aug. 16, 1960 to Merriam et al.

Difficulties are experienced with the application of such thin, adhesive coated transparent film dressings. The film is thin and flexible and will stick to itself. Unless care is taken during application, a smooth dressing which will stay in place is not achieved. In order to overcome some of the problems in separating the film from the release sheets or liners, various proposals have been made. In one proposal, a composite bandage includes a release sheet, an adhesive coated film and a paper framing. The release sheet is peeled off, exposing the adhesive surface. The bandage is held at the paper framing, and the film is applied to the site. The paper framing or border must then be removed or peeled off the film and the film smoothed against the patient's skin. In other forms, adhesive-free tabs are provided to grip and position the dressing. After the film dressing is applied, the tabs are cut or torn from the film.

A need exists for a wound or surgical dressing of thin, adhesive coated film type which is easily applied to the skin and by which the difficulties and problems experienced with even, smooth and secure application are eliminated.

SUMMARY OF THE INVENTION

In accordance with the present invention, the aforementioned needs are fulfilled and application problems are substantially eliminated. Essentially, the wound or surgical dressing includes a film having an adhesive coated surface and which defines opposed edges. The film is covered by a backing, liner or release sheet. Provision is made for increasing the adhesion between the film and the release sheet or sheets at the opposed lateral edges so that the release sheets may be peeled back from the film until the opposed edges of the film are reached. The adhesive coated film may then be applied to the wound site and the lateral edge portions of the film may be separated from the film portion in contact with the patient's skin.

In narrower aspects of the invention, the film is perforated adjacent its lateral edges to facilitate separation of the edge portions when the film is applied to the site.

DETAILED DESCRIPTION OF THE PREFERRED EMBODIMENT

Figure 1:
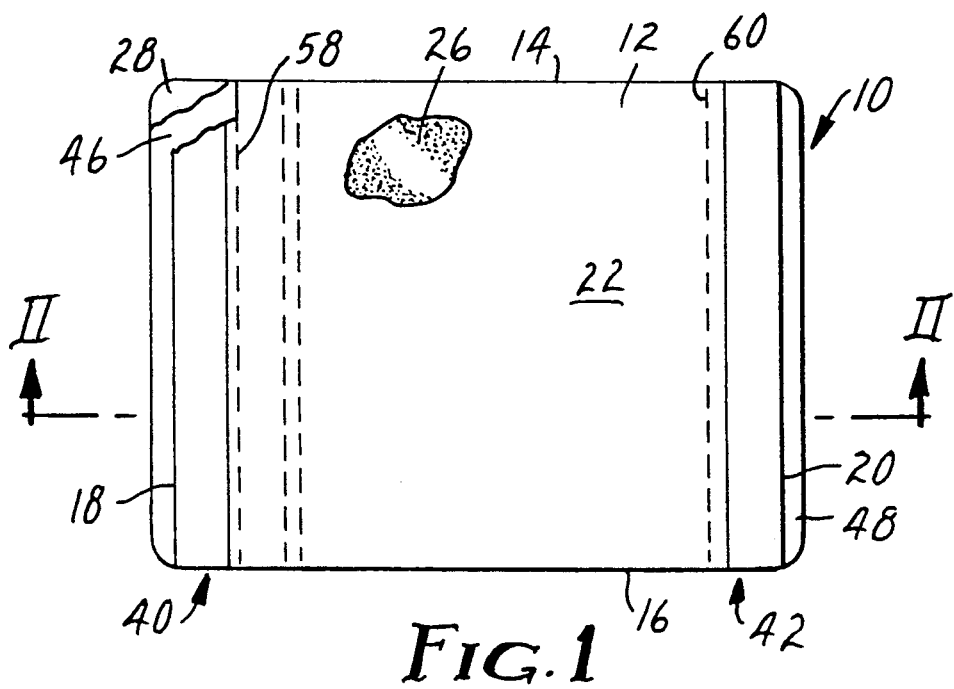
FIG. 1 is a top, plan view of a surgical dressing in accordance with the present invention.
Figure 2:
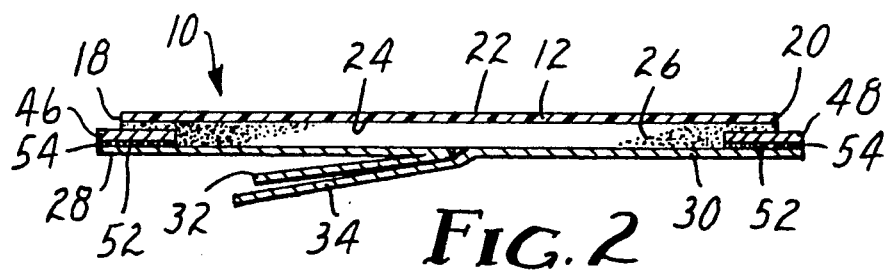
FIG. 2 is a cross-sectional view taken generally along line II—II of FIG. 1.

A preferred embodiment of a wound or surgical dressing in accordance with the present invention is illustrated in FIGS. 1 and 2 and generally designated 10. Dressing 10 includes a generally rectangular sheet of transparent polymeric film 12. Film 12 includes top and bottom edges 14, 16 ad opposed side or lateral edges 18, 20. Film 12 includes a top surface 22 and a bottom surface 24. Surface 24 is coated with a porous, pressure sensitive acrylic adhesive 26. In the embodiment of FIGS. 1 and 2, adhesive coating 26 is applied across the entire area of surface 24.

Dressing 10 further includes a pair of release sheets or liners 28, 30. Liner 28 includes a reverse bent portion or gripping flap 32 which is overlapped by another gripping flap 34 of liner 30. The liners are bent in a plow fold. As shown, liners 28, 30 cover surface 24 of film 12.

Film 12 defines opposed edge portions 40, 42 which extend inwardly from edges 18, 20, respectively. Interposed between portions 40, 42 and the respective liners 28, 30 are adhesion enhancement means or strips 46, 48. Strips 46, 48 extend parallel to edges 18, 20 between top and bottom edges 14, 16. Each strip 46, 48 includes a surface 52 coated with an adhesive 54. Strips 46, 48 secure edge portions 40, 42, respectively, of film 12 to liners 28, 30. Adhesion 26 on film portions 40, 42 has a greater adhesion to the strips than to the liners.

As seen in FIG. 1, bandage 10 is also provided with perforation lines or separating means 58, 60. The perforation lines extend between top and bottom edges 14, 16 of bandage 10 parallel and immediately adjacent the inside edges of adhesive coated strips 46, 48. The perforations extend through the film and may extend into the liners.

While in the broader aspects of the invention many bandage materials could be used for film 12, it is presently preferred that the film be a very thin, transparent polyurethane or transparent matte finish polyether polyurethane medical grade film. The film has a thickness of 1 to 3 mils, depending upon the dressing application. The film is soft, pliable, transparent and gas and vapor permeable. Adhesive 26 may be selected rom one of a wide range of readily available porous, pressure-sensitive acrylic adhesives which are nonirritating and not capable of inducting sensitization in humans. One such film/adhesive combination is available from Avery International, Fasson Industrial Division, Painesville, Ohio, under the brand name MED 5020 polyurethane film. Such film with a thickness of 1 mil and the adhesive with a thickness of 2 mils combination has a moisture vapor transmission rate of 7 grams per 100 inch square per 24 hours at 50 percent relative humidity, 72° F. according to the water method test. The release sheets or liners 28, 30 are commercially available items.

It is presently preferred that liners 28, 30 be a heavyweight white paper coated on both sides with polyethylene for dimensional stability. One side of the liner is overcoated with a silicone release coating to permit ready separation of the adhesive coated film from the liners.

The adhesion enhancement means or strips 46, 48 are commercially available plastic film tapes or commonly referred to as splicing tapes. It is presently preferred that the tapes be a 1 mil thickness polyester film with a silicone rubber adhesive applied to one side. The tape has a total thickness of 2.5 mils, a tensile strength of 25 pounds per inch, an adhesion to steel of 35 ounces per inch and a tack level of 5.4. One such tape is available from The Kendall Company, Polyken Division, Boston, Mass., under the designation Plastic Film Tapes, Tape No. 781. Such splicing tapes are designed for splicing silicone coated materials and hence adhere readily to silicone coated liners 28, 30. Adhesive 26 applied to film 12 has a stronger adherence to the polyester film strips than it does to the silicone coated surface of liners 28, 30.

Figure 3A:
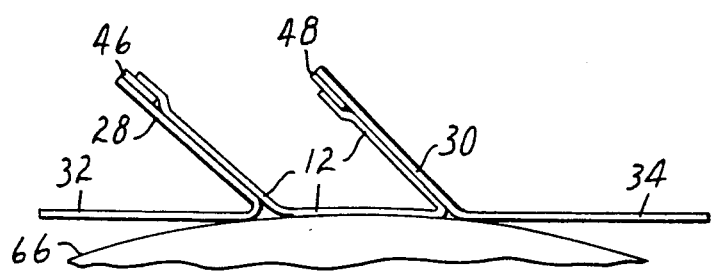
FIGS. 3a–3c are side elevational view showing the application of the surgical dressing in accordance with the present invention to a patient site.
Figure 3B:
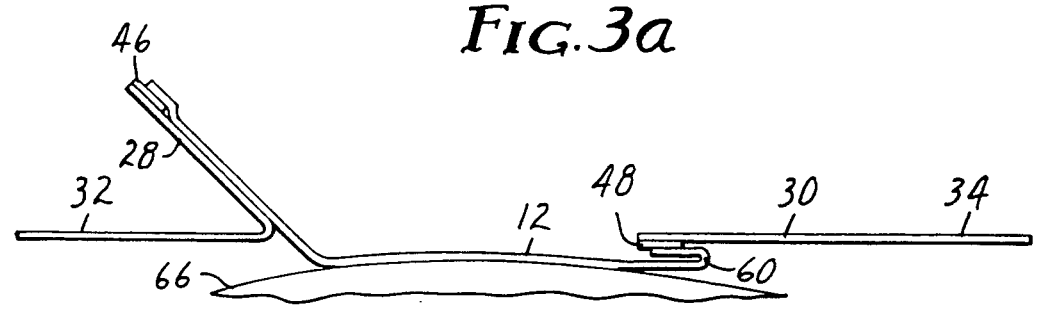
Figure 3C:
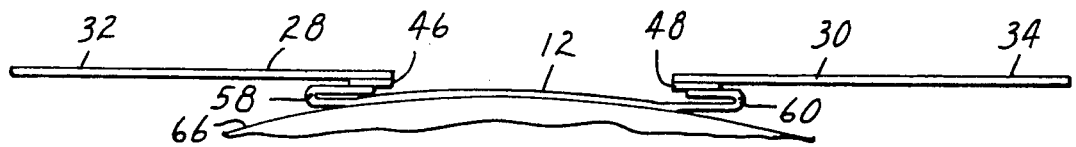

APPLICATION the application of dressing 10 to a patient site is schematically illustrated in FIGS. 3a–3c. As shown in FIG. 3a, by gripping flaps 32, 34, the bandage is initially positioned over the site generally designated 66. Tension may be applied to flap 34 peeling liner 26 from the adhesive coated surface of film 12. Peeling continues until the perforation line 60 at tape strip 48 is reached. Due to the increased adhesion along the strip between the film and the release paper, tension may now be applied to flap 32, as shown in FIGS. 3b and 3c, and film 12 will be peeled away from liner 28 until perforation line 58 at strip 46 is reached. Due to the increased adhesion of the film at strips 46, 48, the film is peeled back from the release liners without separation of the film from the liners until the dressing is positioned completely over the site. The dressing may be smoothed out on the patient's skin. Applying additional tension to gripping flaps 32, 34 causes end portions 40, 42 of the film, strips 46, 48 and liners 26, 28 to tear away from the film in contact with the site along the perforation lines 58, 60. The present invention insures that the thin, pliable and sticky film 12 is maintained in tension and easily peeled back from the liners for ready positioning on the site. The film is in effect supported by the release sheets or liners until it is fully stripped and positioned on the patient. At this point, the edge portions are readily separated from the major portion of the film. A smooth, secure dressing and application results.

The wound dressing or surgical dressing in accordance with the present invention overcomes the problems heretofore experienced with the application of thin polymeric film dressings to the patient's site. The dressing is readily applied without contacting the sterile adhesive coated surface of the film and without danger of the film sticking to itself. A smooth, wrinkle-free application is achieved.

In view of the foregoing description of the preferred embodiment of the present invention, those of ordinary skill in the art will undoubtedly envision various modifications which would not depart from the inventive concepts disclosed herein. It is, therefore, expressly intended that the above description should be considered as only that of the preferred embodiments. The true spirit and scope of the present invention may be determined by reference to the appended claims.

The embodiments of the invention in which an exclusive property or privilege is claimed are defined as follows.

I claim:

1. A wound dressing comprising a film wherein at least one edge of the film is an edge portion which is separable by perforations from the remainder of the film;
   a pressure sensitive adhesive coated on at least a portion of one surface of the film; and
   a liner which is adhered to the edge portion with sufficient tenacity to result in separation along the perforations of the edge portion from the remainder of the film before the liner separates from the edge portion and which liner is releasably adhered to the remainder of the film.

2. The wound dressing of claim 1 wherein the film is a polymeric film.

3. The wound dressing of claim 2 wherein the film is transparent.

4. The wound dressing of claim 3 wherein the film has two edge portions at opposing edges of the film and the liner is comprised of at least a first liner and a second liner wherein the first segment is adhered to one edge portion and the second segment is adhered to the opposing edge portion.

5. A method of applying a thin flexible adhesive coated film to a substrate wherein the film has an edge portion along at least one edge thereof which is separable from the remainder of the film and a liner adhered to the adhesive-coated surface of the film which liner is adhered to the edge portion of the film with sufficient tenacity to result in separation of the edge portion from the remainder of the film before the liner edge portion bond fails and which is releasably adhered to the remainder of the film comprising:
   removing the liner from the substrate contacting surface of film;
   placing the substrate contacting surface in intimate contact with the substrate; and
   separating the liner and edge portion from the film.

6. A wound dressing comprising a film wherein at least one edge of the film is an edge portion which is separable by perforations from the remainder of the film;

a pressure sensitive adhesive coated on at least a portion of one surface of the film; and a liner which is adhered to the edge portion by means of a strip of splicing tape having an adhesive coated surface contacting said liner and another adhesive coated surface contacting said edge portion, said splicing tape adhering said liner and said edge portion together with sufficient tenacity to result in separation along the perforations of the edge portion from the remainder of the film before the liner separates from the edge portion and which liner is releasably adhered to the remainder of the film.

7. The wound dressing of claim 6 wherein the film has two edge portions at opposing edges of the film and the liner is comprised of at least a first liner and a second liner wherein the first segment is adhered to one edge portion by one strip of splicing tape and the second segment is adhered to the opposing edge portion by another strip of splicing tape.

8. The wound dressing of claim 6 wherein said splicing tape comprises a polyester film having a silicone rubber adhesive coating.

9. The wound dressing of claim 6 wherein said film is a transparent polyurethane material.

10. The wound dressing of claim 6 wherein said pressure sensitive adhesive coated on said film is an acrylate adhesive.

* * * * *